United States Patent [19]
Fujiwara et al.

[11] Patent Number: 5,853,612
[45] Date of Patent: Dec. 29, 1998

[54] COMPOUND FOR USE IN LIQUID CRYSTAL COMPOSITION, LIQUID CRYSTAL COMPOSITION COMPRISING THE SAME, AND LIQUID CRYSTAL DISPLAY DEVICE USING THE SAME

[75] Inventors: Hidenori Fujiwara, Kakegawa; Kazuya Nagao, Kawagoe, both of Japan

[73] Assignee: Hoechst Aktiengesellschaft, Frankfurt, Germany

[21] Appl. No.: 977,929

[22] Filed: Nov. 24, 1997

Related U.S. Application Data

[63] Continuation of Ser. No. 665,006, May 15, 1996, abandoned, which is a continuation of Ser. No. 362,010, Dec. 22, 1994, abandoned.

[30] Foreign Application Priority Data

Dec. 27, 1993 [JP] Japan .................................. 5-333181

[51] Int. Cl.⁶ .......................... C09K 19/34; C07D 307/02
[52] U.S. Cl. ........................ 252/299.61; 549/505
[58] Field of Search ................... 252/299.61; 549/29, 549/505

[56] References Cited

U.S. PATENT DOCUMENTS

| | | | |
|---|---|---|---|
| 4,290,905 | 9/1981 | Kanbe | 252/299.63 |
| 4,764,619 | 8/1988 | Gunjima et al. | 546/226 |
| 4,965,018 | 10/1990 | Uchida et al. | 252/299.61 |

OTHER PUBLICATIONS

Chem. Abstracts 100:121044.

*Primary Examiner*—C. H. Kelly
*Attorney, Agent, or Firm*—Frommer Lawrence & Haug LLP

[57] ABSTRACT

Novel compounds which increase a response speed of a liquid crystal composition by mixing with a liquid composition are represented by the general formula (I):

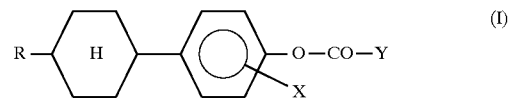

wherein R represents an alkyl group having from 1 to 10 carbon atoms, X represents a hydrogen atom, a methyl group, an ethyl group or a halogen atom, and Y represents an unsubstituted aromatic heterocyclic ring.

6 Claims, 2 Drawing Sheets

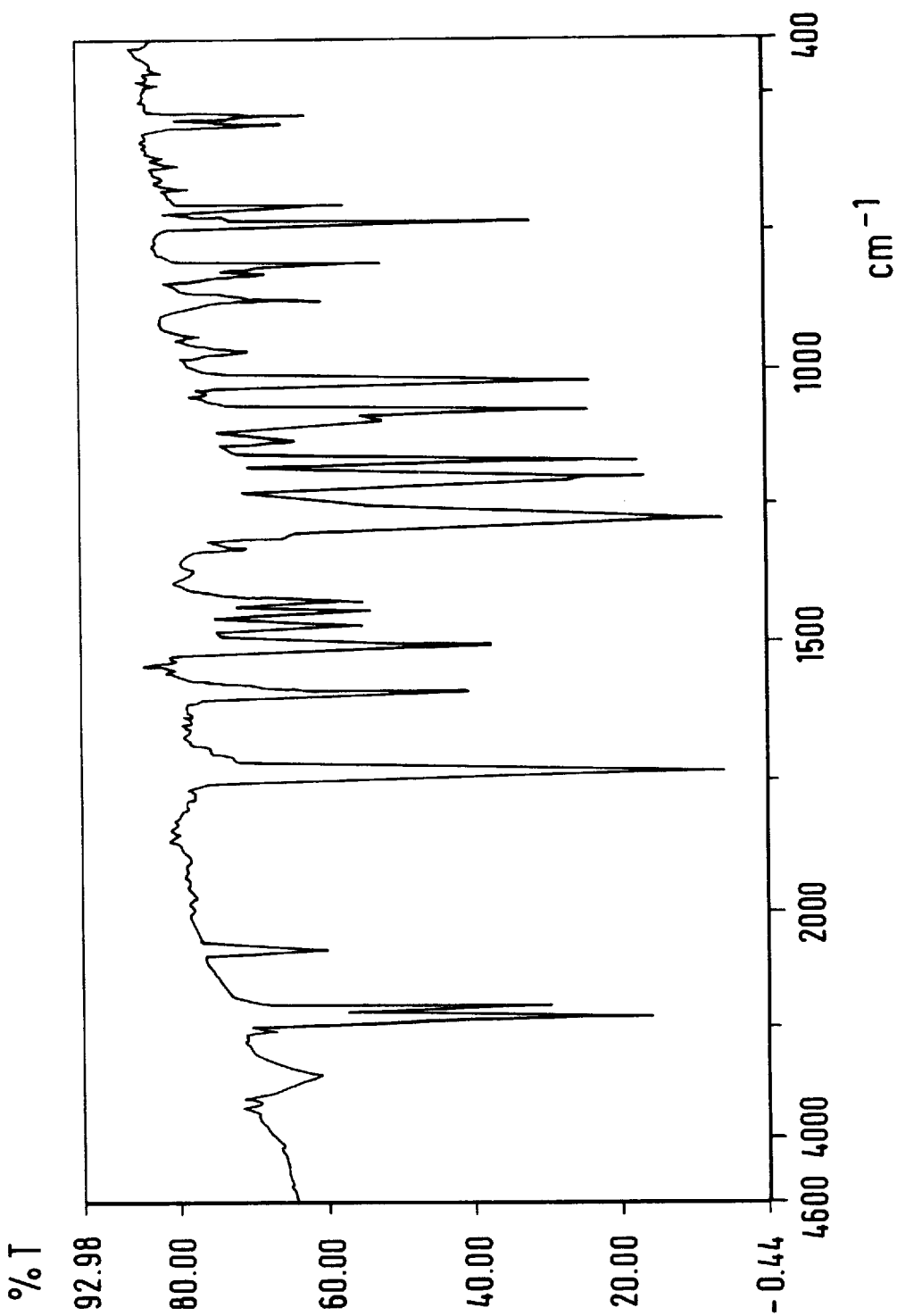

COMPOUND FOR USE IN LIQUID CRYSTAL COMPOSITION, LIQUID CRYSTAL COMPOSITION COMPRISING THE SAME, AND LIQUID CRYSTAL DISPLAY DEVICE USING THE SAME

This application is a continuation of application Ser. No. 08/665,006, filed May 15, 1996, which is abandoned, which is a continuation of application Ser. No. 08/362,010, filed Dec. 22, 1994, abandoned.

BACKGROUND OF THE INVENTION

In particular in the last decade, liquid crystals have been introduced into various technical areas where electro-optical and display device properties are required (for example in watch, calculator and typewriter displays). These display devices are based on the dielectric alignment effects in the nematic, cholesteric and/or smectic phases of the liquid-crystalline compounds, where, caused by the dielectric anisotropy, the molecular long axes of the compounds adopt a preferred alignment in an applied electric field. The conventional response times in these display devices are too long for many other potential areas of application of liquid crystals. This disadvantage is particularly noticeable if a large number of pixels have to be addressed. The production costs of equipment containing relatively large screen areas are then generally too high.

In addition to nematic and cholesteric liquid crystals, optically active smectic liquid-crystal phases have also been increasing in importance for a few years.

Clark and Lagerwall have been able to show that the use for ferroelectric liquid-crystal systems in very thin cells give electro-optical switch or display elements which have response times faster by a factor of up to 1000 compared with conventional TN ("twisted nematic") cells (cf., for example, Lagerwall et al., "Ferroelectric Liquid Crystals for Displays", SID Symposium, October Meeting 1985, San Diego, Calif., USA). Due to these and other favorable properties, for example the possibility for bistable switching and the contrast which is virtually independent of the viewing angle, FLCs are fundamentally very suitable for the abovementioned areas of application, for example via matrix addressing. Due to their high contrast and speed, ferroelectric liquid crystals are also particularly suitable in the area of spatial light modulators (cf., for example, U. Efron in "Spatial Light Modulators and Applications", SPIE, Vol. 1150, p. 46 ff). However, ferroelectric liquid-crystal mixtures are generally not fast enough to drive, for example, high-resolution, fast display elements. It is therefore desirable to find components which increase the response speed of liquid-crystalline mixtures. The invention therefore relates to components which shorten the response time of liquid-crystal mixtures.

Liquid crystal molecules comprising only one side chain are described in EP-A 0 541 081. Such compounds are useful for increasing the response speed of liquid crystal mixtures.

SUMMARY OF THE INVENTION

Surprisingly it has now been found that the compounds of the formula (I), comprising only one side chain, which are not specifically disclosed in the European patent application, do not only drastically increase the response speed of liquid crystal mixtures but also lower the melting point of such mixtures. This even holds true, when the mixture in question already comprises compounds with only one side chain as disclosed in EP-A 0 541 081.

Therefore, the present invention provides a novel compound represented by the following formula (I):

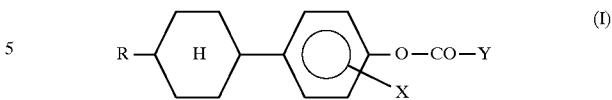

wherein R represents an alkyl group having from 1 to 10 carbon atoms, X represents a hydrogen atom, a methyl group, an ethyl group or a halogen atom, an Y represents an unsubstituted aromatic heterocyclic ring. The compound is a PCH (phenylcyclohexane) type one-wing liquid crystal compound characterized in that an alkyl or alkoxy chain is not attached to the Y side.

BRIEF DESCRIPTION OF THE DRAWINGS

The following detailed description, given by way of example but not intended to limit the invention solely to the specific embodiments described, may best be understood in conjunction with the accompanying drawings, in which:

FIG. 2 shows IR data of a novel compound of the present invention, 4-(n-pentylcyclohexyl)phenyl 3-pyridinecarboxylate.

DESCRIPTION OF THE PREFERRED EMBODIMENTS

Figure 1:
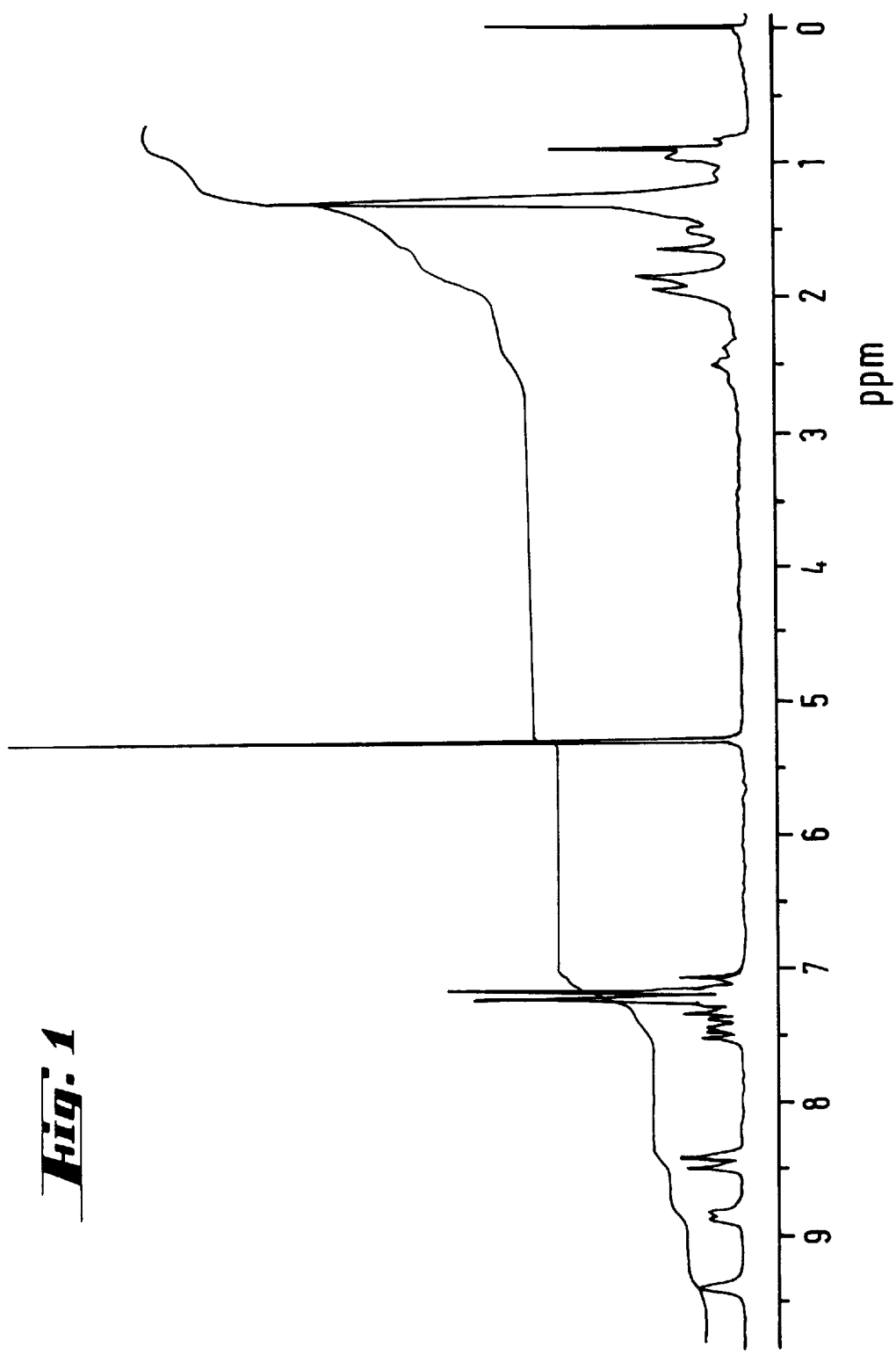
FIG. 1 shows NMR data of a novel compound of the present invention, 4-(n-pentylcyclohexyl)phenyl 3-pyridinecarboxylate.

Preference is given to compounds of the formula (I), where R is a straight chain alkyl group having from 1 to 10 carbon atoms, X is a hydrogen atom, a methyl group, an ethyl group, F or Cl, and Y is pyridine, furan or thiophene.

Particular preference is given to compounds of the formula (I) where R is an n-pentyl group, X is a hydrogen atom, and Y is pyridine.

The compounds of the present invention can be prepared by a process which is known in literature references. (For example, reference can be made to Houben-Weyl, Methoden der Organischen Chemie, Georg-Thieme-Verlag, Stuttgart; K. Dimitrowa, J. Hauschild, H. Zaschke and H. Schubert, Journal für praktische Chemie, Vol. 322 (1980), p. 933; and H. Zaschke and H. Schubert, Journal für praktische Chemie, Vol. 315 (1973), p. 315.)

Further, the present invention provides a liquid crystal composition comprising at least one, in particular one to five, of the compounds represented by the above-described general formula (I), and a liquid crystal display device comprising the liquid crystal composition.

The compound of the formula (I) according to the present invention is suitable as a component of a liquid crystal composition, in particular, ferroelectic liquid crystal composition. The liquid crystal composition comprises the component of the present invention in an amount of from 0.01 to 60% by weight, preferably from 0.1 to 40% by weight, more preferably from 0.1 to 20% by weight. Other components are preferably selected from known compounds having nematic, cholesteric or smectic phases, for example, Schiff bases, biphenyl, terphenyl, phenylcyclohexane, cyclohexylbiphenyl or heterocyclic compounds containing N, S, and/or O such as pyrimidine, cinnamates, cholesterol esters or various crosslinked polycyclic esters of p-alkylbenzoic acids having a terminal polar group.

Surprisingly, it has now been found that the addition of the compound of formula (I) considerably increases the response speed of liquid crystal compositions, even compositions already comprising compounds disclosed in EP-A 0 541 081, and at the same time lower the melting points of such compositions.

These compositions can be used, in display devices, switching elements, optical modulators, elements for image processing, signal processing, or electrooptical or completely optical elements in the field of non-linear optics.

The present invention is further described in more detail by the following examples.

In the ferroelectric liquid crystal composition, the electric response time τ (μs) was measured at 25° C. The phase transition temperature was determined by observing changes in the texture upon heating by a polarizing microscope. The melting point was measured using a DSC apparatus. The phase transition temperatures between each of the following phases: nematic (N or N*), smectic-C ($S_C$ or $S_C$*), smectic-A ($S_A$) and crystal (X) are represented by °C., and shown between the symbols of the phases in the phase system.

EXAMPLE 1

Synthesis of 4-(n-pentylcyclohexyl)phenyl 3-pyridinecarboxylate 5.0 g (20.29 mmol) of 4-(trans-n-pentylcyclohexyl)phenol, 2.75 g (22.32 mmol) of 3-pyridinecarboxylic acid and 0.25 g (2.03 mmol) of 4-N,N-dimethylaminopyridine (DMAP) were dissolved in 70 ml of toluene and cooled to 0° to 5° C. To the resulting solution was added dropwise 4.6 g of dicyclohexyl carbodiimide (DCC) dissolved in 20 ml of toluene. After stirring at 0° C. for 30 minutes, the mixture was stirred at room temperature for 7 hours. The precipitated urea derivative was filtered off, and the organic layer was washed with a 5% acetic acid solution and then with a saturated aqueous sodium chloride solution. After drying over anhydrous magnesium sulfate, the solvent was distilled off to obtain 7.2 g of a crude product. The product was purified by silica gel column chromatography and recrystallization from ethanol, and 4.7 g of 4-(trans-n-pentylcyclohexyl)phenyl 3-pyridinecarboxylate was obtained. Yield, 66.6%. Melting point, 93.0° to 94.0° C. The phase transition temperatures of the resulting compound were as follows:

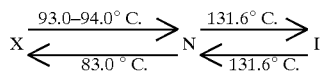

The results of the measurement of NMR and IR spectra are shown in FIG. 1 and FIG. 2, respectively.

EXAMPLE 2

Synthesis of 4-(n-pentylcyclohexyl)phenyl 4-pyridinecarboxylate 5.0 g (20.29 mmol) of 4-(trans-n-pentylcyclohexyl)phenol, 2.75 g (22.32 mmol) of 4-pyridinecarboxylic acid and 0.25 g (2.03 mmol) of 4-N,N-dimethylaminopyridine (DMAP) were dissolved in 70 ml of toluene and cooled to 0° to 5° C. To the resulting solution was added dropwise 4.6 g of DCC dissolved in 20 ml of toluene. After stirring at 0° C. for 30 minutes, the mixture was stirred at room temperature for 7 hours. The precipitated urea derivative was filtered off, and the organic layer was washed with a 5% acetic acid solution and then with a saturated aqueous sodium chloride solution. After drying over anhydrous magnesium sulfate, the solvent was distilled off to obtain 7.0 g of a crude product. The product was purified by silica gel column chromatography and recrystallization from ethanol, and 3.1 g of 4-(trans-n-pentylcyclohexyl)phenyl 4-pyridinecarboxylate was obtained. Yield, 43.5%. Melting point, 103.6°–106.8° C. The phase transition temperatures of the resulting compound were as follows:

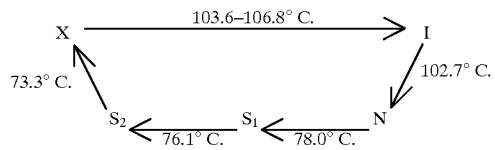

EXAMPLE 3

Synthesis of 4-(n-pentylcyclohexyl)phenyl 2-pyridinecarboxylate 5.0 g (20.29 mmol) of 4-(trans-n-pentylcyclohexyl)phenol, 2.75 g (22.32 mmol) of 2-pyridinecarboxylic acid and 0.25 g (2.03 mmol) of 4-N,N-dimethylaminopyridine (DMAP) were dissolved in 70 ml of toluene and cooled to 0° to 5° C. To the resulting solution was added dropwise 4.6 g of DCC dissolved in 20 ml of toluene. After stirring at 0° C. for 30 minutes, the mixture was stirred at room temperature for 7 hours. The precipitated urea derivative was filtered off, and the organic layer was washed with a 5% acetic acid solution and then with a saturated aqueous sodium chloride solution. After drying over anhydrous magnesium sulfate, the solvent was distilled off to obtain 7.1 g of a crude product. The product was purified by silica gel column chromatography and recrystallization from ethanol, and 3.6 g of 4-(trans-n-pentylcyclohexyl)phenyl 2-pyridinecarboxylate was obtained. Yield, 51%. Melting point, 148° C. The phrase transition temperatures of the resulting compound were as follows:

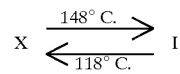

EXAMPLE 4

Synthesis of 4-(n-pentylcyclohexyl)phenyl 2-thiophenecarboxylate 5.0 g (20.29 mmol) of 4-(trans-n-pentylcyclohexyl)phenol, 2.75 g (22.32 mmol) of 2-thiophenecarboxylic acid and 0.25 g (2.03 mmol) of 4-N,N-dimethylaminopyridine (DMAP) were dissolved in 70 ml of toluene and cooled to 0° to 5° C. To the resulting solution was added dropwise 4.6 g of DCC dissolved in 20 ml of toluene. After stirring at 0° C. for 30 minutes, the mixture was stirred at room temperature for 7 hours. The precipitated urea derivative was filtered off, and the organic layer was washed with a 5% acetic acid solution and then with a saturated aqueous sodium chloride solution. After drying over anhydrous magnesium sulfate, the solvent was distilled off to obtain 7.2 g of a crude product. The product was purified by silica gel column chromatography and recrystallization from ethanol, and 3.0 g of 4-(trans-n-pentylcyclohexyl)phenyl 2-thiophenecarboxylate was obtained. Yield, 66.6%. Melting point, 110° C. The phase transition temperatures of the resulting compound were as follows:

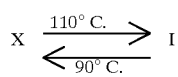

EXAMPLE 5

Synthesis of 4-(n-pentylcyclohexyl)phenyl 2-furoric Acid Ester 5.0 g (20.29 mmol) of 4-(trans-n-pentylcyclohexyl) phenol was dissolved in 60 ml of pyridine and cooled to 5° C. To the solution was added dropwise 2.91 g of furoyl chloride, and the mixture was stirred at room temperature for 4 hours. Then, the reaction solution was poured into 100 ml of ice-water, and the precipitated crystal was filtered and purified by silica gel column chromatography and recrystallization from ethanol. 3.0 g of 4-(trans-n-pentylcyclohexyl)phenyl 2-furoric acid ester was obtained. Yield, 3.4%. Melting point, 116° C. The phase transition temperatures of the resulting compound were as follows:

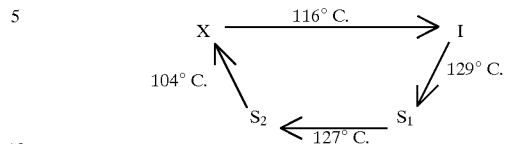

EXAMPLE 6

The liquid crystal composition (A) containing no liquid crystal molecule according to the present invention has the following composition (%).

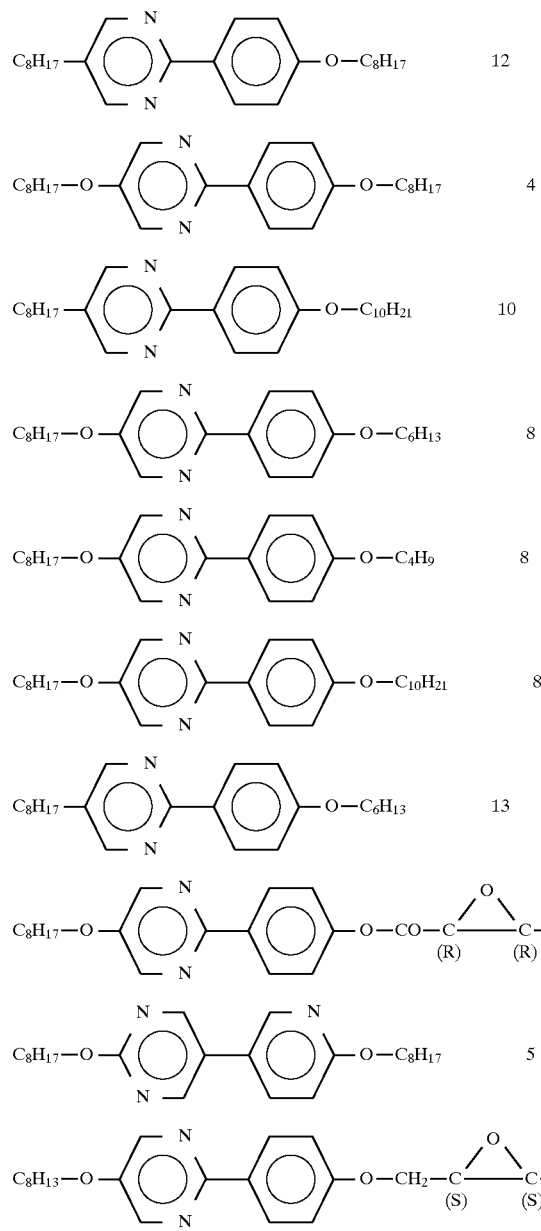

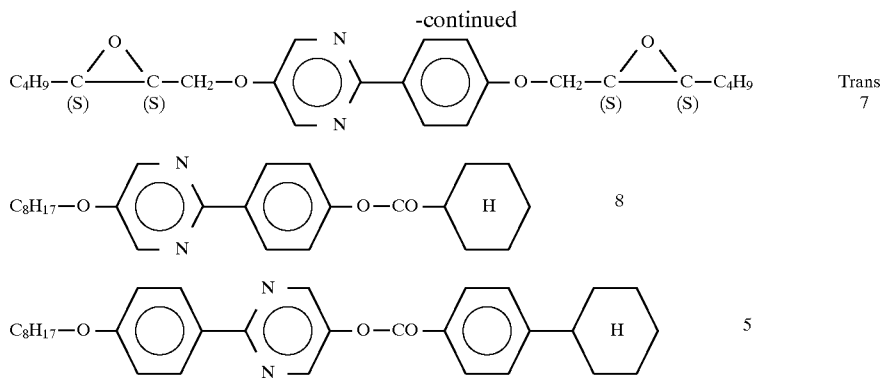

A liquid crystal composition (C) containing 95% of the liquid crystal composition (A) and 5% of the liquid crystal molecule (B) of Example 1, and a liquid crystal composition (E) containing 98% of the liquid crystal composition (A) and 2% of the liquid crystal molecule (D) of Example 2 were prepared. The phase transition temperatures of these liquid crystal compositions were as follows.

TABLE 1

| | Phase Transition Temperature | | | |
|---|---|---|---|---|
| | X | $S_C$ | $S_A$ | N | I |
| Composition (A) | −7 | 66 | 80 | 85 |
| Composition (C) | −10 | 46 | 76 | 83 |
| Composition (E) | −9 | 53 | 78 | 83 |

As shown in Table 1, the melting points were lowered as indicated above by addition of the liquid crystal compound (B) or (D) according to the present invention.

EXAMPLE 7

Each of the liquid crystal compositions (A), (C) and (E) of Example 6 was filled in a cell having a thickness of 1.6 μm, and a response time in an applied electric field of 15 V/μm was measured. The response time of the liquid crystal composition (A) was 30 μsec, while the response time of the liquid crystal compositions (C) and (E) were 18 μsec and 26 μsec, respectively. The results showed that the response to a bipolar pulse was increased by adding the liquid crystal compound (B) or (D) of the present invention.

We claim:

1. A compound of the general formula (I):

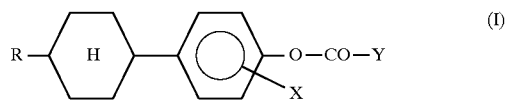

wherein R represents an alkyl group having from 1 to 10 carbon atoms, X represents a hydrogen atom, a methyl group, an ethyl group or a halogen atom and Y presents furan-2-yl.

2. The compound as claimed in claim 1, wherein the symbols in the formula (I) have the following meanings:

$R^1$ is a straight chain alkyl group having from 1 to 10 carbon atoms;

X is a hydrogen atom, a methyl group, an ethyl group, F or Cl; and

Y is furan-2-yl.

3. A liquid crystal composition comprising at least one compound of the general formula (I) as claimed in claim 1.

4. A liquid crystal display device comprising the liquid crystal composition as claimed in claim 3.

5. The liquid crystal composition as claimed in claim 3, which is ferroelectric.

6. The liquid crystal display as claimed in claim 4, comprising from 0.01 to 60% by weight of a compound of the general formula (I).

* * * * *